United States Patent
Almariego et al.

(10) Patent No.: US 9,198,901 B2
(45) Date of Patent: Dec. 1, 2015

(54) TRIS(HYDROXYMETHYL)AMINOMETHANE SALTS OF A SMALL-MOLECULE GLP1R AGONIST AND PHARMACEUTICAL COMPOSITIONS AND USES THEREOF

(71) Applicant: TransTech Pharma, LLC, High Point, NC (US)

(72) Inventors: Danilo Almariego, High Point, NC (US); Dharma Rao Polisetti, High Point, NC (US); Eric Benjamin, Jamestown, NC (US); Hassan El Abdellaoui, Jamestown, NC (US); Soumya P. Sahoo, Portland, ME (US)

(73) Assignee: vTv Therapeutics LLC, High Point, NC (US)

( * ) Notice: Subject to any disclaimer, the term of this patent is extended or adjusted under 35 U.S.C. 154(b) by 0 days.

(21) Appl. No.: 14/489,890

(22) Filed: Sep. 18, 2014

(65) Prior Publication Data
US 2015/0005339 A1 Jan. 1, 2015

Related U.S. Application Data

(63) Continuation of application No. PCT/US2013/033091, filed on Mar. 20, 2013.

(60) Provisional application No. 61/614,265, filed on Mar. 22, 2012.

(51) Int. Cl.
| | | |
|---|---|---|
| *A61K 31/5365* | (2006.01) | |
| *C07D 265/28* | (2006.01) | |
| *A61K 31/4375* | (2006.01) | |
| *C07D 491/04* | (2006.01) | |
| *B01J 2/02* | (2006.01) | |

(52) U.S. Cl.
CPC .............. *A61K 31/4375* (2013.01); *B01J 2/02* (2013.01); *C07D 491/04* (2013.01)

(58) Field of Classification Search
CPC .......................... A61K 31/5365; C07D 265/28
See application file for complete search history.

(56) References Cited

U.S. PATENT DOCUMENTS

| | | |
|---|---|---|
| 7,727,983 B2 | 6/2010 | Mjalli et al. |
| 7,790,714 B2 | 9/2010 | Mjalli et al. |
| 7,906,507 B2 | 3/2011 | Mjalli et al. |
| 8,524,708 B2 | 9/2013 | Mjalli et al. |
| 8,703,766 B2 | 4/2014 | Mjalli et al. |
| 8,933,222 B2 | 1/2015 | Mjalli et al. |
| 2010/0022601 A1 | 1/2010 | Ogawa et al. |
| 2010/0324033 A1* | 12/2010 | Mjalli et al. ............... 514/229.8 |
| 2011/0064806 A1 | 3/2011 | Polisetti et al. |
| 2015/0087640 A1 | 3/2015 | Mjalli et al. |

FOREIGN PATENT DOCUMENTS

WO WO 2009/111700 9/2009

OTHER PUBLICATIONS

Freeman, Jennifer L.R. et al., "TTP3859: Identification of a Non-Peptide GLP-1 Receptor Agonist That Enhances Glycemic Control in vivo," 4th G Protein-Coupled Receptors: An ASPET Colloquium, Apr. 24-25, 2013, abstract, p. 51 (2013).

Freeman, Jennifer L.R. et al., "TTP3859: Identification of a Non-Peptide GLP-1 Receptor Agonist That.Enhances Glycemic Control in vivo," 4th G Protein-Coupled Receptors: An ASPET Colloquium, Apr. 24-25, 2013, poster 61 (2013).

Wootten, Denise et al., "Differential Activation and Modulation of the Glucagon-Like Peptide-1 Receptor by Small Molecule Ligands" Molecular Pharmacology, vol. 83, pp. 822-834 (2013).

* cited by examiner

*Primary Examiner* — Samantha Shterengarts
(74) *Attorney, Agent, or Firm* — Sameul B. Rollins

(57) ABSTRACT

The invention provides tris(hydroxymethyl)aminomethane salts of a small-molecule GLP1R agonist. The invention further provides solid compositions comprising tris(hydroxymethyl)aminomethane salts of a small-molecule GLP1R agonist. The invention further provides uses of tris(hydroxymethyl)aminomethane salts of a small-molecule GLP1R agonist, e.g., for treating type 1 diabetes, type 2 diabetes, or obesity.

20 Claims, No Drawings

TRIS(HYDROXYMETHYL)AMINOMETHANE SALTS OF A SMALL-MOLECULE GLP1R AGONIST AND PHARMACEUTICAL COMPOSITIONS AND USES THEREOF

FIELD OF INVENTION

The invention provides tris(hydroxymethyl)aminomethane salts of a small-molecule GLP1R agonist. The invention further provides solid compositions comprising tris(hydroxymethyl)aminomethane salts of a small-molecule GLP1R agonist. The invention further provides uses of tris(hydroxymethyl)aminomethane salts of a small-molecule GLP1R agonist, e.g., for treating type 1 diabetes, type 2 diabetes, or obesity.

DESCRIPTION OF RELATED ART

Type 2 diabetes is a metabolic disorder where the disease progression may be characterized by one or more of the following: peripheral tissue insulin resistance, hyperglycemia, islet b-cell compensation, hyperinsulinemia, dyslipidemia, increased liver gluconeogenesis, or ultimate loss of b-cell mass and function. The pathophysiological consequences of aberrant glucose and lipid metabolism are toxicity to organs such as the kidney, eye, peripheral neurons, vasculature, and heart. Thus, there is a need for agents that may delay disease progression by improving glycemic control and by improving b-cell mass and function.

Glucagon-like peptide-1 (GLP1) is a member of the incretin family of neuroendocrine peptide hormones secreted from L-cells of the intestine in response to food ingestion. GLP1 has multiple metabolic effects that are attractive for an antidiabetic agent. A key function of GLP1 is to activate its receptor, GLP1R, on the pancreatic b-cell to enhance glucose-dependent insulin secretion. Positive metabolic benefits of GLP1 may include, but are not limited to, suppression of excessive glucagon production, decreased food intake, delayed gastric emptying, and improvement of b-cell mass and function. The positive effects of GLP1 on b-cell mass and function offers the prospect that GLP1-based therapies may delay early-stage disease progression. In addition, a GLP1R agonist may also be useful in combination therapies, such as with insulin in patients with type 1 diabetes. Unfortunately, the rapid proteolysis of GLP1 into an inactive metabolite limits its use as a therapeutic agent.

Validation of GLP1R agonists as a therapeutic modality was achieved by Exendin-4 (BYETTA, Amylin Pharmaceuticals, Inc.), a peptide GLP1 receptor agonist recently approved in some countries for the treatment of type 2 diabetes. Dosing of Exendin-4 by subcutaneous administration lowers blood glucose and decreases HbA1c levels, which are important biomarker measurements for disease control. Thus, an oral GLP1 receptor agonist should provide glycemic control while offering the convenience of oral dosing.

The GLP1 receptor (GLP1R) belongs to the class B receptor sub-class of the G protein-coupled receptor (GPCR) superfamily that regulates important physiological and patho-physiological processes. In addition to the seven transmembrane domains characteristic of all GPCR family members, class B GPCRs contain a relatively large N-terminal domain. It is believed that the binding and activation of these receptors by large natural peptide ligands require both the N-terminal domain and the transmembrane domain of the receptor. The identification of low-molecular-weight non-peptide molecules that bind and activate class B GPCRs has proven to be difficult.

Because peptides, such as GLP1, may lack sufficient oral bioavailability for consideration as oral drug agents, small molecule modulators of GLP1R with oral bioavailability are desired. WO 2009/111700 describes various small-molecule GLP1R agonists, such as (S)-3-(4'-cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid, which is hereinafter identified as "oxadiazoanthracene derivative 1" or "ODAAD1".

BRIEF SUMMARY OF THE INVENTION

In one aspect, the invention provides tris(hydroxymethyl)aminomethane ("tris") salts of ODAAD1, referred to as "tris-ODAAD1 salts".

In another aspect, the invention provides pharmaceutical compositions comprising a tris-ODAAD1 salt. In some embodiments, the pharmaceutical composition comprises a pharmaceutically acceptable carrier, excipient, or diluent.

In another aspect, the invention provides methods of treating type 2 diabetes by administering to a subject (e.g., a human) a tris-ODAAD1 salt.

In another aspect, the invention provides methods of treating type 1 diabetes by administering to a subject (e.g., a human) a tris-ODAAD1 salt.

In another aspect, the invention provides methods of lowering blood-glucose in a subject by administering to a subject (e.g., a human) a tris-ODAAD1 salt.

In another aspect, the invention provides methods of treating obesity in a subject by administering to a subject (e.g., a human) a tris-ODAAD1 salt.

In another aspect, the invention provides methods of slowing gastric emptying by administering to a subject (e.g., a human) a tris-ODAAD1 salt.

In another aspect, the invention provides methods of lowering an HbA1c level by administering to a subject (e.g., a human) a tris-ODAAD1 salt.

In another aspect, the invention provides methods of increasing glucose-dependent insulin secretion by administering to a subject (e.g., a human) a tris-ODAAD1 salt.

In another aspect, the invention provides methods of suppressing glucagon secretion by administering to a subject (e.g., a human) a tris-ODAAD1 salt.

In another aspect, the invention provides methods of treating an eating disorder by administering to a subject (e.g., a human) a tris-ODAAD1 salt.

In another aspect, the invention provides methods of modulating a human GLP1 receptor by administering to a subject (e.g., a human) a tris-ODAAD1 salt.

Additional features and aspects of the present invention are described hereinafter.

BRIEF DESCRIPTION OF DRAWINGS

Not applicable.

DETAILED DESCRIPTION

Small-molecule GLP1R agonists, such as ODAAD1, may be useful in treating diabetes because they may activate the GLP1 receptor, GLP1R, on the pancreatic b-cell to enhance glucose-dependent insulin secretion in a subject. Small-molecule GLP1R agonists have the additional advantage that they may have higher oral bioavailability than protein-based GLP1R agonists.

ODAAD1 and Salts with Tris(Hydroxymethyl)Aminomethane

ODAAD 1 is a small-molecule GLP 1R agonist. The compound and its synthesis are described in WO 2009/111700. Tris(hydroxymethyl)aminomethane ("tris"), also known as THAM or tromethamine, is an organic compound.

In one aspect, the invention provides tris(hydroxymethyl) aminomethane ("tris") salts of ODAAD1, referred to as "tris-ODAAD1 salts". As used herein, the term "salt" or "salts" has its standard and customary meaning in the pharmaceutical arts. A general description of pharmaceutical salts is available in Berge et al., *J. Pharm. Sci.,* 66: 1-19 (1977). In general, the invention provides tris-ODAAD 1 salts in a solid-state form. The solid-state form of the salt may be amorphous, crystalline, or partly crystalline. In addition, the invention is not limited to any particular quantity of the solid, and can include amounts as small as a single pairing of two counterions. In a tris-ODAAD1 salt, the tris(hydroxymethyl)aminomethane molecule bears at least a partial positive charge, while the ODAAD1 molecule bears at least a partial negative charge. In some embodiments, the ratio of tris to ODAAD1 in the salt is from 0.80 to 1.20 (i.e., from 0.80:1 to 1.20:1), or from 0.90 to 1.10, or from 0.95 to 1.05, or from 0.97 to 1.03, or from 0.99 to 1.01, based on total number of molecules of each counterion present in a given sample. In some embodiments, the ratio of tris to ODAAD 1 in the salt is 1:1, based on total number of molecules of each counterion present in a given sample. A 1:1 tris-ODAAD 1 salt may alternately be referred to as a "mono-tris salt of ODAAD1".

The tris-ODAAD1 salts of the invention may exist in the presence of other solid-state forms of ODAAD1. For example, a tris-ODAAD1 salt may exist in a solid composition, where the solid composition also comprises the free acid/base of ODAAD1 or may also comprise other salted forms of ODAAD1 (e.g., a hydrochloride salt of ODAAD1). In some embodiments, the invention provides a solid composition comprising a tris-ODAAD1 salt, where at least 25%, or at least 40%, or at least 50%, or at least 60%, or at least 70%, or at least 80%, or at least 90%, or at least 95%, or at least 97%, or at least 99% of the ODAAD1 molecules (in both free and salted forms) in the solid composition are in the form of a tris-ODAAD1 salt.

Solid Compositions Comprising a Tris-ODAAD1 Salt

In another aspect, the invention provides solid compositions comprising a tris-ODAAD1 salt. As used herein, the term "solid composition" refers to any solid-state composition that is, or can be made into, a solid pharmaceutical dosage form. Thus, in some embodiments, the solid compositions are bulk powders comprising a tris-ODAAD1 salt. In other embodiments, however, the solid compositions are in a dosage form suitable for oral administration to a subject, such as a capsule, microcapsule, nanocapsule, tablet, suspension, sachet, and the like, where said dosage forms comprise a tris-ODAAD1 salt. Moreover, the term "solid" does not necessarily imply a complete absence of liquid or gaseous media. For example, solids can have various interstices, which may partially or fully fill with other gaseous and/or liquid media. Thus, the invention includes solid compositions that are suspended (i.e., remain at least partially, if not substantially, insoluble) in liquid media, such as syrups, elixirs, and the like.

The solid compositions of the invention may include a tris-ODAAD1 salt in any suitable amount. In some embodiments, a tris-ODAAD1 salt is present in a therapeutically effective amount. As used herein, the term "therapeutically effective amount" refers to an amount of a tris-ODAAD1 salt that elicits the biological or medicinal response in a tissue, system, or subject that is being sought by a researcher, veterinarian, medical doctor, patient or other clinician, which includes reduction or alleviation of the symptoms of the disease being treated.

As used herein, the term "subject" includes, for example, horses, cows, sheep, pigs, mice, dogs, cats, and primates such as chimpanzees, gorillas, rhesus monkeys, and humans. In some embodiments, the subject is a human. In some embodiments, the subject exhibits symptoms of type 2 diabetes.

The actual amount of a tris-ODAAD1 salt required, e.g., for treatment of any particular subject, will depend upon a variety of factors, including the following: the disorder being treated; its severity; the specific solid composition employed; the age, body weight, general health, gender, and diet of the subject; the mode of administration; the time of administration; the route of administration; the rate of excretion of the therapeutic agent; the duration of the treatment; any drugs used in combination or coincidental with the therapeutic agent; and other such factors well known to those skilled in the art. In various embodiments, for example, the solid composition may contain 1 mg or more, 5 mg or more, 10 mg or more, 20 mg or more, 40 mg or more, 50 mg or more, 100 mg or more, 200 mg or more, 300 mg or more, 400 mg or more, or 500 mg or more of a tris-ODAAD1 salt in a given dosage form. In some embodiments, for example, the solid composition may contain less than 400 mg of a tris-ODAAD1 salt, or less than 800 mg of a tris-ODAAD1 salt in a given dosage form. In some further embodiments, the solid composition may contain about 50 mg, or about 100 mg, or about 150 mg, or about 200 mg, or about 250 mg, or about 300 mg, or about 350 mg, or about 400 mg, or about 450 mg, or about 500 mg of a tris-ODAAD1 salt in a given dosage form. In some further embodiments, the solid composition may contain between 5 mg and 500 mg, or between 25 mg and 250 mg of a tris-ODAAD1 salt in a given dosage form.

Tris-ODAAD1 salts (according to any of the above embodiments) may be useful for treating a variety of diseases or conditions where activation of GLP1R is beneficial. Thus, the solid compositions of the invention, when administered to a subject, e.g., in a therapeutically effective amount, are useful for treating type 1 diabetes, type 2 diabetes, metabolic syndrome, obesity, glucose intolerance, hyperglycaemia, dyslipidemia, hypertriglyceridemia, syndrome X, insulin resistance, impaired glucose tolerance (IGT), obesity, diabetic dyslipidemia, hyperlipidemia, arteriosclerosis, atherosclerosis, other cardiovascular diseases, hypertension, metabolic disorders where activation of GLP 1R is beneficial, or complications resulting from or associated with diabetes, including, but not limited to, neuropathy, retinopathy, nephropathy, and impaired wound healing.

In some embodiments, the solid composition of the invention is a pharmaceutical composition. As used herein, the term "pharmaceutical composition" refers to a solid composition (e.g., a powder) that contains a pharmaceutically active ingredient (e.g., ODAAD1 or a salt thereof) and at least a carrier, diluent, or excipient, where none of the ingredients in the solid composition is generally biologically undesirable at the administered quantity.

The tris-ODAAD 1 salt may be combined in a pharmaceutical formulation with a pharmaceutically acceptable carrier, diluent, or excipient in any suitable manner. In some embodiments, the tris-ODAAD1 salt is uniformly distributed throughout the pharmaceutical composition. For example, the solid-state dried tris-ODAAD1 salt may be dry-mixed with other solid-state ingredients until the distribution of the ingredients within the mixture is uniform. In other embodiments, the tris-ODAAD1 salt may not be distributed uniformly throughout the pharmaceutical composition, e.g., where the pharmaceutical composition includes multi-layer granules whose layers have different concentrations of the tris-ODAAD1 salt.

The pharmaceutical composition comprising the tris-ODAAD1 salt may or may not be applied to a carrier or binder. In some embodiments, for example, the tris-ODAAD1 salt is introduced into the pharmaceutical composition without a carrier, e.g., as a dried powder of tris-ODAAD1 salt. In other embodiments, the tris-ODAAD1 salt is applied to a carrier or a binder. In embodiments where the tris-ODAAD1 salt is applied to a carrier or a binder, the tris-ODAAD1 salt may be applied to the carrier or binder by any suitable means, including, but not limited to, wet granulation, spray granulation, or spray drying.

Water-Soluble Surfactant

In some embodiments of the invention, the solid composition comprises a tris-ODAAD1 salt (according to any of the above embodiments), and further comprises a water-soluble surfactant. Surfactants are generally known in the art. Water-soluble surfactants are surfactants that dissolve in water when used at a desired concentration. Water-soluble surfactants, as a class, are well known in the art. The water-soluble surfactant may be selected from any suitable surfactant, including, but not limited to sulfuric acid alkyl ester salts, such as sodium lauryl sulfate; bile acid salts, such as sodium taurocholate and sodium glycocholate; propylene glycol fatty acid mono- or diesters, such as those sold under the trade name MIGLYOL® 840 (Sasol Olefins and Surfactants, Houston, Tex., USA); polyethylene glycol fatty acid esters, such as polyethylene glycol monooleate and polyethylene glycol monostearate; polysorbates, such as polyoxyethylene sorbitan fatty acid esters sold under the trade names TWEEN 20, TWEEN 40, and TWEEN 80 (Spectrum Chemicals, Gardena, Calif., USA); polyoxyethylene-polyoxypropylene copolymer and block copolymer surfactants, such as poloxamer 188, poloxamer 235, poloxamer 404, and poloxamer 407 and those sold under the trade names PLURONIC F87, PLURONIC F127, PLURONIC F68, PLURONIC L44, PLURONIC P123, and PLURONIC P85 (BASF, Mt. Olive, N.J., USA); polyoxyethylene derivatives of natural oils and waxes, such as polyoxyethylene castor oil and polyoxyethylene hydrogenated castor oil, for example those sold under the trade names CREMOPHOR RH40 and CREMOPHOR EL (BASF, Mt. Olive, N.J., USA); polyoxyethylene derivatives of tocopherols or tocotrienols, such as vitamin E d-alpha tocopheryl polyethyleneglycol succinate (Vitamin E TPGS); and sorbitan fatty acid esters, such as sorbitan monooleate, sorbitan monostearate, sorbitan monopalmitate, sorbitan monolaurate, and sorbitan monocaprylate, sold under the trade names SPAN 80, SPAN 60, SPAN 40, SPAN 20, and SEFSOL 418, respectively (Croda International PLC, Goole, UK). The selection and amount of the water soluble surfactant may be based, in part, upon its compatibility with the other ingredients in the solid composition, the amount of a tris-ODAAD1 salt, the form of the tris-ODAAD1 salt (e.g., crystalline, etc.), and the consideration that the water-soluble surfactant is not generally deleterious to a human subject when the solid composition containing the surfactant is administered at typical dosing quantities. In some embodiments, the water-soluble surfactant is a polyoxyethylene sorbitan fatty acid ester, e.g., polysorbate 80. In some embodiments, the water-soluble surfactant is sodium lauryl sulfate. In some embodiments, the water-soluble surfactant is vitamin E d-alpha tocopheryl polyethyleneglycol succinate (vitamin E TPGS). In some embodiments, the water-soluble surfactant is a mixture of one or more of a polyoxyethylene sorbitan fatty acid ester, sodium lauryl sulfate, or vitamin E TPGS.

As used herein, the term "a mixture of" or "a mixture thereof" refers to any mixture of two or more materials and/or compositions that would be encompassed within the list that follows or precedes the phrase, respectively. The phrase does not refer to any particular type of mixture. Thus, the "mixture" is not necessarily an intimate mixture, a homogeneous mixture, etc. Furthermore, the "mixture" need not contain a representative of each element in the list. For example, if a composition comprises "A, B, C, or a mixture thereof," the term contemplates mixtures of A and B (with no C present), mixtures of B and C (with no A present), mixtures of A and C (with no B present), as well as mixtures of A, B, and C. As a further illustration, suppose that A, B, or C define generic categories (e.g., a polysorbate), where, for example, $A^1$ and $A^2$ are species or subgenuses encompassed by the genus A. In that instance, if a composition comprises "A, B, C, or a mixture thereof," the term also contemplates mixtures of $A^1$ and $A^2$ (where no B and no C are present in the mixture).

The solid composition may comprise any suitable amount of water-soluble surfactant. The amount of water-soluble surfactant may depend on a variety of factors, including, but not limited to, the identity of the water-soluble surfactant, the identity and concentrations of other ingredients in the solid composition, and the like. In some embodiments, the solid composition comprises between 0.1% and 10% by weight, or between 0.1% and 7% by weight, or between 0.3% and 5% by weight, or between 0.5% and 3.5% by weight, or between 1.0% and 3.0% by weight, or between 1.5% and 2.5% by weight, of water-soluble surfactant, based on the total weight of the solid composition. In some embodiments, the solid composition comprises about 0.5% by weight, or about 1% by weight, or about 1.5% by weight, or about 2% by weight, or about 2.5% by weight, or about 3% by weight, or about 3.5% by weight, or about 4% by weight, or about 5% by weight, of water-soluble surfactant, based on the total weight of the solid composition. In some further embodiments, the weight/weight ratio of tris-ODAAD1 salt to surfactant in the solid composition is between 10:1 and 1:1, or between 8:1 and 2:1, or between 6:1 and 3:1, or about 5:1. In some further embodiments, the weight/weight ratio of tris-ODAAD1 salt to surfactant in the evaporation residue of the solid composition is between 10:1 and 1:1, or between 8:1 and 2:1, or between 6:1 and 4:1, or about 5:1.

As noted below, in some embodiments, the solid composition comprises an evaporation residue. In some such embodiments, the evaporation residue comprises a water-soluble surfactant (according to any of the above embodiments).

Pharmaceutically Acceptable Basic Excipient

In some embodiments of the invention, the solid composition comprises a tris-ODAAD1 salt and, optionally, a water-soluble surfactant (according to any of the above embodiments), and further comprises a pharmaceutically acceptable basic excipient. As used herein, the term "pharmaceutically acceptable basic excipient" refers to any metal salt of an acid which demonstrates basic properties, in either the Bronsted or Lewis sense, which includes those salts where all protons have been replaced with a mono or polyvalent metal ion and extends to those metal salts of acids which contain a proton but would lead to an aqueous solution having a pH greater than 7 when dissolved in water in appreciable amounts. Many such salts, particularly those of inorganic acids and many organic acids, may be water soluble. But water solubility is not a limiting factor in selecting a basic excipient. Metal salts of surfactants, whether water-soluble or water dispersible, are also within the scope of the basic excipients as defined herein.

The pharmaceutically acceptable basic excipients of the invention are generally regarded as safe, at least in the dosage amounts used.

Pharmaceutically acceptable basic excipients include, but are not limited to, any of the salts of inorganic acids, short-chain mono-, di-, or tri-carboxylic acids, or salts of the various long-chain fatty acids or sulfonated fatty acids and alcohols and related surfactants. Selected salts should be inert in the sense that they themselves would not be expected or intended to demonstrate any deleterious or untoward pharmacological effects on the subject to which the dosage forms are administered.

Pharmaceutically acceptable basic excipients of inorganic acids include, for example: basic alkali metal salts of phosphoric acid, such as disodium phosphate, dipotassium phosphate, and calcium phosphate; basic alkali metal salts of orthophosphate, hypophosphate, and pyrophosphate, such as the di- and tri-sodium forms of orthophosphate, the di- and tri-potassium orthophosphates, magnesium orthophosphate, and magnesium pyrophosphate, sodium or potassium hypophosphate, sodium or potassium pyrophosphate, calcium hypophosphate and calcium orthophosphate, including the mono, di- and tri-calcium forms, calcium pyrophosphate, and mixed alkali metal salts of these various phosphates; alkali metal salts of nitric acids, such as sodium nitrate, potassium nitrate, calcium nitrate, and magnesium nitrate; alkali metal salts of sulfuric acid, such a sodium sulfate, potassium sulfate, magnesium sulfate, and calcium sulfate, and alkali metal salts of boric acid, such as sodium borate or potassium borate.

Pharmaceutically acceptable basic excipients further include basic alkali metal salts of various mono-, di-, or tri-carboxylic acids, for example, the alkali metal salts of carbonic acid, such as sodium bicarbonate, sodium carbonate, potassium carbonate, potassium bicarbonate, sodium potassium carbonate, magnesium carbonate or calcium carbonate may be used herein.

Pharmaceutically acceptable basic excipients further include alkali metal salts and alkaline earth metal salts of organic acids, such as formic acid, acetic acid, propionic acid, glycolic acid, lactic acid, pyruvic acid, oxalic acid, malonic acid, succinic acid, malic acid, maleic acid, fumaric acid, tartaric acid, benzoic acid, cinnammic acid, and mandelic acid.

As noted above, in some embodiments of the invention, solid compositions comprising a tris-ODAAD 1 salt and, optionally, a water-soluble surfactant (according to any of the embodiments recited above) and at least one pharmaceutically acceptable basic excipient. In some such embodiments, the pharmaceutically acceptable basic excipient is selected from trisodium phosphate, potassium carbonate, sodium carbonate, sodium bicarbonate, potassium bicarbonate, or a mixture thereof. In other such embodiments, the pharmaceutically acceptable basic excipient is a mixture of sodium carbonate and sodium bicarbonate. In some other such embodiments, the pharmaceutically acceptable basic excipient is sodium carbonate. In some other such embodiments, the pharmaceutically acceptable basic excipient is sodium bicarbonate.

In various embodiments, the pharmaceutically acceptable basic excipient is present in the solid composition in an amount such that the relative amount of pharmaceutically acceptable basic excipient to a tris-ODAAD1 salt is suitable to allow for effective dissolution of the tris-ODAAD1 salt in the stomach and/or the upper part of the small intestine. The suitable ratio of the tris-ODAAD1 salt to the pharmaceutically acceptable basic excipient can depend on various factors, including but not limited to: the presence or absence of other excipients (and their relative quantities) in the solid composition; the dosage form in which the solid composition is packaged; the chemical identity of the pharmaceutically acceptable basic excipient (including the $pK_b$ value(s)); the process for preparing the solid composition; and the total amount of the tris-ODAAD1 salt present in the dosage form. In some embodiments, the weight/weight ratio of the tris-ODAAD1 salt to the pharmaceutically acceptable basic excipient in the solid composition ranges from 5:1 to 1:10, or from 2:1 to 1:7, or from 1:1 to 1:5, or from 1:2 to 1:4, or from 1:3 to 1:10, or from 1:4 to 1:8. The amount of pharmaceutically acceptable basic excipient may also vary, in part, depending upon the particular basic excipient chosen.

Binder

In some embodiments of the invention, the solid composition comprises a tris-ODAAD1 salt and, optionally, a water-soluble surfactant (according to any of the above embodiments), and further comprises a binder. Suitable binders include, but are not limited to, polyvinylpyrrolidone (PVP), hydroxypropylmethyl cellulose acetate succinate (HPMCAS), hydroxypropylmethyl cellulose phthalate (HPMCP), hydroxypropylmethyl cellulose (HPMC), poloxamers, hydroxypropyl methyl cellulose acetate, hydroxypropyl cellulose, and hydroxyethyl cellulose acetate, polyacrylates, methyl acrylatemethacrylic acid copolymers, ethyl acrylate-methacrylic acid copolymers, cellulose acetate phthalate, cellulose acetate trimellitate, carboxymethyl ethyl cellulose, hydroxyethyl cellulose (HEC), polyethylene oxide (polyox), polyethylene glycol, ethylcellulose, and mixtures thereof.

In some embodiments, the binder is hydroxypropylmethyl cellulose acetate succinate (HPMCAS) or polyvinylpyrrolidone (PVP) or hydroxypropylmethylcellulose (HPMC). In some embodiments, the binder is hydroxypropylmethyl cellulose acetate succinate (HPMCAS). In some embodiments, the binder is polyvinylpyrrolidone (PVP). In some embodiments, the binder is hydroxypropylmethylcellulose (HPMC).

In some embodiments of the invention, the amount of binder present in a solid composition is an amount such that the weight/weight ratio of the tris-ODAAD 1 salt to binder ranges from 3:1 to 1:3, or from 2:1 to 1:2, or from 3:2 to 2:3. In some embodiments, the weight/weight ratio of the tris-ODAAD1 salt to binder in the solid composition is about 1.2:1, or about 1.1:1, or about 1:1, or about 1:1.1, or about 1:1.2. The amount of binder in a solid composition of the invention may vary depending, in part, upon the specific features of the solid composition, including the amount of the tris-ODAAD1 salt.

In other embodiments of the invention, the amount of binder present in the evaporation residue of the solid composition is an amount such that the weight/weight ratio of the tris-ODAAD1 salt to binder ranges from 3:1 to 1:3, or from 2:1 to 1:2, or from 3:2 to 2:3. In some embodiments, the weight/weight ratio of the tris-ODAAD1 salt to binder in the evaporation residue of the solid composition is about 1.2:1, or about 1.1:1, or about 1:1, or about 1:1.1, or about 1:1.2.

Evaporation Residue

In some embodiments of the invention, the solid compositions comprise an evaporation residue, which comprises a tris-ODAAD1 salt (according to any of the embodiments recited above). In some such embodiments, the evaporation residue further comprises other excipients. In some such embodiments, the evaporation residue comprises a tris-ODAAD1 salt and a water-soluble surfactant (according to any of the embodiments recited above). In some further such embodiments, the evaporation residue comprises a tris-ODAAD1 salt, a water-soluble surfactant, and one or both of a pharmaceutically acceptable basic excipient and/or a binder (each according to any of the embodiments recited above). In other embodiments, the evaporation residue comprises a tris-ODAAD1 salt, but does not contain any substantial amount of pharmaceutically acceptable basic excipient (e.g., less than 5% by weight, or less than 3% by weight, or less than 1% by weight, or less than 0.5% by weight, of the total weight of the evaporation residue).

As used herein, the term "evaporation residue" refers to the solids remaining after the substantial removal of solvent from a solution and/or suspension comprising a tris-ODAAD1 salt, alone or in combination with other components. For example, the evaporation residue contains less than 1% by weight, or less than 0.5% by weight, or less than 0.2% by weight of solvent, based on the total weight of the evaporation residue. In some embodiments, removal of the solvent from the solution or suspension comprises spray drying the solution or suspension to form a powder. In other embodiments, the solution is removed by evaporation, for example by using a rotovap or a flat-bed dryer to form an evaporation residue.

Additional Ingredients

In some embodiments of the invention, the solid composition further comprises at least one additional pharmaceutical ingredient. As used herein, the term "additional pharmaceutical ingredient" refers to a component or excipient other than powdered pharmaceutically acceptable carriers, so long as the material is not generally deleterious to a human subject when the solid composition is administered at dosing quantities. Non-limiting examples of additional ingredients include:

a) glidants and lubricants, such as colloidal silica, talc, magnesium stearate, calcium stearate, stearic acid, solid polyethylene glycol, sodium oleate, sodium stearate, sodium benzoate, sodium acetate, sodium chloride, sodium stearyl furamate, and sodium lauryl sulfate;

b) disintegrating and solubilizing agents, such as agar-agar, calcium carbonate, sodium carbonate, croscarmellose sodium, starches, pregelatinized starches, sodium starch glycolate, crospovidone, methyl cellulose, agar, bentonite, xanthan gum, alginic acid, and certain silicates;

c) solution retarding agents, such as polymers, for example biodegradable polymers such as polylactic acid, polyepsilon caprolactone, polyhydroxy butyric acid, polyorthoesters, polyacetals, polydihydropyrans, polycyanoacrylates, and cross-linked or amphipathic block copolymers of hydrogelsparaffin, and wax, for example, paraffin;

d) resorption accelerating agents, such as quaternary ammonium compounds;

e) absorption agents, such as quaternary ammonium compounds, bentonite, kaolin, or dicalcium phosphate;

f) fillers, such as anhydrous lactose, microcrystalline cellulose, mannitol, calcium phosphate, pregelatinized starch, and sucrose.

It is within the ability of one of skill in the art to select the at least one additional pharmaceutical ingredient and the amount of the additional ingredient(s). The selection and amount of the at least one additional pharmaceutical ingredient is based, in part, upon its compatibility with the other ingredients in the formulation, the amount of the tris-ODAAD1 salt in the solid composition, and consideration that it is not generally deleterious to a human subject when the solid composition is administered at dosing quantities.

Methods of Making the Solid Composition

The pharmaceutical compositions of the invention can be made by various means known in the pharmaceutical formulation arts. Suitable methods include, but are not limited to the following: wet granulation methods, including standard wet granulation techniques, and specialized wet granulation techniques, such as high-shear mixture granulation, fluid-bed granulation, extrusion, and spheronization, spray granulation (e.g., spray-drying granulation), and the like; dry granulation techniques, including standard dry granulation and specialized dry granulation techniques, such as slugging, roller compaction, and the like; steam granulation techniques; melt granulation techniques, such as thermoplastic melt granulation; moisture-activated dry granulation techniques (MADG); moist granulation techniques (MGT); thermal adhesion granulation processes (TAGP); foam granulation techniques; and the like. In some embodiments of the invention, a wet granulation technique is used to make a pharmaceutical composition comprising a tris-ODAAD1 salt (according to any of the embodiments recited above). In some embodiments, a fluid-bed wet granulation technique is used to make a solid composition comprising a tris-ODAAD 1 salt (according to any of the embodiments recited above). In some embodiments, a spray granulation technique is used to make a solid composition comprising a tris-ODAAD1 salt (according to any of the embodiments recited above). In some embodiments, a spray drying technique is used to make a solid composition comprising a tris-ODAAD1 salt (according to any of the embodiments recited above).

The aforementioned techniques may generate a solid composition that comprises granules that contain a tris-ODAAD1 salt (according to any of the embodiments recited above). The particle size and the distribution of particle sizes of the granules can be adjusted according to known techniques to achieve release profiles, dissolution, and the like. In some such embodiments, at least 80%, or at least 85%, or at least 90%, or at least 95%, or at least 98% (by weight) of said granules have a particle size that is between 1 µm and 1 mm. Further, in some such embodiments, at least 80%, or at least 85%, or at least 90%, or at least 95%, or at least 98% (by weight) of said granules have a particle size that is between 1 µm and 500 µm.

Spray Granulation

In some embodiments, the tris-ODAAD1 is applied to a carrier by spray granulation techniques. Such spray granulation techniques are well known within the pharmaceutical arts. In general, spray granulation involves spraying a liquid solution onto a solid powder, which typically causes powder particles to agglomerate lightly. In most instances, the drying occurs during the agglomeration process, although it can be desirable, in some instances, to dry the resulting granules to drive out residual moisture (e.g., in a fluid bed). Following granule formation, the granules can be sized (using, e.g., mesh screens). In some instances, the granules are milled, so as to achieve a desired size.

Spray granulation techniques may employ a binder solution or suspension, which is sprayed onto solid particles. The binder solution or suspension contains a binder material and other materials dissolved or suspended in a solvent. Once the solvent evaporates, the remaining components in the binder solution or suspension form an evaporation residue, as described above. Acceptable solvents include, but are not limited to, water or other polar solvents such as alcohols, for example ethanol and isopropanol, ketones, for example acetone, and mixtures thereof. In various embodiments, the solvent is selected from water, ethanol, acetone or mixtures thereof. In some embodiments, the solvent is water. In other embodiments, the solvent is a less polar solvent, such as THF.

The binder solution or suspension may comprise a binder. In some embodiments, the binder solution or suspension also comprises a tris-ODAAD1 salt. In some such embodiments, the binder solution or suspension further comprises other excipients. In some further embodiments, the evaporation residue of any of the aforementioned embodiments may or may not further comprise a binder.

Suitable binders include, but are not limited to, polyvinylpyrrolidone (PVP), hydroxypropylmethyl cellulose acetate succinate (HPMCAS), hydroxypropylmethyl cellulose phthalate (HPMCP), hydroxypropylmethyl cellulose (HPMC), poloxamers, hydroxypropyl methyl cellulose acetate, hydroxypropyl cellulose, and hydroxyethyl cellulose acetate, polyacrylates, methyl acrylatemethacrylic acid copolymers, ethyl acrylatemethacrylic acid copolymers, cellulose acetate phthalate, cellulose acetate trimellitate, carboxymethyl ethyl cellulose, hydroxyethyl cellulose (HEC), polyethylene oxide (polyox), polyethylene glycol, ethylcellulose, and mixtures thereof.

In some embodiments, the binder is hydroxypropylmethyl cellulose acetate succinate (HPMCAS) or polyvinylpyrrolidone (PVP) or hydroxypropylmethylcellulose (HPMC). In some embodiments, the binder is HPMCAS. In other embodiments, the binder is PVP. In other embodiments, the binder is HPMC.

In some embodiments, the spray granulation process comprises spraying a solution or suspension onto a solid pharmaceutically acceptable carrier. As used herein and as known in the art, the term "pharmaceutically acceptable carrier" refers to pharmaceutically acceptable basic excipients, as described herein, pharmaceutically acceptable inert carriers, and/or mixtures thereof. As used herein and as known in the art, the term "pharmaceutically acceptable inert carriers" refers to those inorganic and organic carriers that are physiologically harmless and are not basic excipients. In addition to the pharmaceutically acceptable basic excipients listed above, solid pharmaceutically acceptable carriers include, but are not limited to edible carbohydrates, for example, starches, lactose, sucrose, glucose, and mannitol, silicic acid, calcium carbonate, calcium phosphate, sodium phosphate, crospovidone, and kaolin.

Spray Drying

In some embodiments, the tris-ODAAD1 is applied to a carrier (e.g., a binder) by spray drying techniques. Such spray drying techniques are well known within the pharmaceutical arts. In general, spray drying involves spraying a liquid solution or suspension into a chamber. In general, the droplet size and chamber conditions are set so as to induce the evaporation of the solvent following the spraying of the solution into the chamber. As the solvent evaporates, an evaporation residue remains. In many instances, the drying occurs before the sprayed solution reaches the bottom of the chamber, although it can be desirable, in some instances, to dry the resulting evaporation residue to drive out residual moisture (e.g., in a fluid bed). Then, the evaporation particles can be sized (using, e.g., mesh screens), if desired. In some instances, the evaporation residue particles are milled, so as to achieve a desired size.

Spray drying techniques generally employ a binder solution or suspension, which is sprayed into the chamber. The binder solution or suspension contains a binder material and other materials dissolved or suspended in a solvent. Once the solvent evaporates, the remaining components in the binder solution or suspension form an evaporation residue. Acceptable solvents include, but are not limited to, water or other polar solvents such as alcohols, for example ethanol and isopropanol, ketones, for example acetone, and mixtures thereof. In various embodiments, the solvent is selected from water, ethanol, acetone or mixtures thereof. In some embodiments, the solvent is water. In other embodiments, the solvent is a less polar solvent, such as THF.

In some embodiments, the binder solution or suspension also comprises a tris-ODAAD1 salt. In some such embodiments, the binder solution or suspension further comprises a surfactant. In some further embodiments, the evaporation residue of any of the aforementioned embodiments may or may not further comprise a binder.

Suitable binders include, but are not limited to, polyvinylpyrrolidone (PVP), hydroxypropylmethyl cellulose acetate succinate (HPMCAS), hydroxypropylmethyl cellulose phthalate (HPMCP), hydroxypropylmethyl cellulose (HPMC), poloxamers, hydroxypropyl methyl cellulose acetate, hydroxypropyl cellulose, and hydroxyethyl cellulose acetate, polyacrylates, methyl acrylatemethacrylic acid copolymers, ethyl acrylatemethacrylic acid copolymers, cellulose acetate phthalate, cellulose acetate trimellitate, carboxymethyl ethyl cellulose, hydroxyethyl cellulose (HEC), polyethylene oxide (polyox), polyethylene glycol, ethylcellulose, and mixtures thereof.

In some embodiments, the binder is hydroxypropylmethyl cellulose acetate succinate (HPMCAS) or polyvinylpyrrolidone (PVP) or hydroxypropylmethylcellulose (HPMC). In some embodiments, the binder is HPMCAS. In other embodiments, the binder is PVP. In other embodiments, the binder is HPMC.

Dosage Forms

The invention further provides solid compositions in forms for oral administration, for example, as discrete units, such as capsules or tablets. Preparation of the solid compositions in forms intended for oral administration is within the ability of one skilled in the art, including the selection of pharmaceutically acceptable additional ingredients from the groups listed above in order to provide pharmaceutically elegant and palatable preparations. For example, the solid compositions of the invention may be prepared by methods known in the pharmaceutical formulation art, for example, see Remington's Pharmaceutical Sciences, 18th ed., (Mack Publishing Company, Easton, Pa., 1990).

In various embodiments, capsules may be prepared by, for example, preparing a powder mixture comprising a tris-ODAAD1 salt and encapsulating the powder with gelatin or some other appropriate shell material. Additional ingredients, such as those set forth above and including glidants and lubricants and disintegrating and solubilizing agents, may be added to the powder before the encapsulation.

In various other embodiments, tablets may be prepared by, for example, preparing a powder mixture, such as that described above in various embodiments, and pressing the mixture into tablets. Additional ingredients, such as those set forth above and including glidants and lubricants, disintegrating and solubilizing agents, binders, solution retardants, and absorption agents, may be added to the powder before pressing into tablets. The powder mixture may be wet-granulated with a binder such as syrup, starch paste, acadia mucilage or solutions of cellulosic or polymeric materials, and forcing through a screen. Or, in other embodiments, the powder mixture may be run through the tablet machine, producing slugs broken into granules. Then granules may be lubricated and then compressed into tablets. In a further embodiment, the powder mixture may be compressed directly into tablets without granulation or slugging.

In some embodiments of the invention, the tablets are multipart or multilayer tablets. For example, the tris-ODAAD1 and at least one additional ingredient, are compressed to form one part or one layer of a multipart or multilayer tablet. At least one pharmaceutically acceptable basic excipient is compressed to form another part or another layer of a multipart or multilayer tablet. In at least one embodiment, the tris-ODAAD1 salt part or layer and the basic excipient part or layer are combined to form a multipart or multilayer tablet. In a further embodiment, the tris-ODAAD1 salt part or layer and the basic excipient part or layer are separated by an additional part or layer comprising additional ingredients, e.g., ingredients that may react with or that may decrease the stability of the tris-ODAAD1 salt.

The tablets of the invention may be either uncoated or coated. In various embodiments, tablets are coated with a clear or opaque protective coating, which may for example, comprise a sealing coat of shellac, a coating of sugar or polymeric material, and/or a polish coating of wax. In various embodiments, tablets are coated to delay disintegration and absorption in the gastrointestinal tract and thereby provide a sustained action over a longer period. Such coatings may comprise glyceryl monostearate or glyceryl distearate. Additionally, dyestuffs can be added to these coatings to distinguish different unit dosages.

In any embodiment where a tris-ODAAD1 salt is included in a pharmaceutical composition, such pharmaceutical compositions may be in a form suitable for oral use, for example, as tablets, troches, lozenges, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

The solid compositions of the invention may exhibit improved bioavailability or improved stability relative to solid compositions that do not contain ODAAD1 in the form of a tris salt, or relative to solid compositions that do not contain ODAAD1 in the form of a tris salt and also do not contain a binder.

Dosage Quantities

In embodiments of the invention, an amount of ODAAD1 (or a salt thereof) is administered to a subject (e.g., a human). The amount of ODAAD1 (or a salt thereof) administered may vary depending on various factors, including but not limited to, the weight of the subject, the nature and/or extent of the subject's disease, etc. In some embodiments, ODAAD1 (or a salt thereof) is administered to a subject (e.g., a human) in an amount that ranges from 10 mg/day to 1000 mg/day, or from 25 mg/day to 800 mg/day, or from 37 mg/day to 750 mg/day, or from 75 mg/day to 700 mg/day, or from 100 mg/day to 600 mg/day, or from 150 mg/day to 500 mg/day, or from 200 mg/day to 400 mg/day.

Methods of Treatment

Tris-ODAAD1 salts may be useful for treating a variety of diseases or conditions where activation of GLP1R is beneficial. Thus, the solid compositions of the invention, when administered to a subject, e.g., in a therapeutically effective amount, are useful for treating type 1 diabetes, type 2 diabetes, metabolic syndrome, obesity, glucose intolerance, hyperglycaemia, dyslipidemia, hypertriglyceridemia, syndrome X, insulin resistance, impaired glucose tolerance (IGT), obesity, diabetic dyslipidemia, hyperlipidemia, arteriosclerosis, atherosclerosis, other cardiovascular diseases, hypertension, metabolic disorders where activation of GLP1R is beneficial, or complications resulting from or associated with diabetes, including, but not limited to, neuropathy, retinopathy, nephropathy, and impaired wound healing.

In one aspect, the invention provides methods of treating type 2 diabetes by administering to a subject (e.g., a human) a tris-ODAAD1 salt according to any of the embodiments described in the foregoing sections.

In another aspect, the invention provides methods of treating type 1 diabetes by administering to a subject (e.g., a human) a tris-ODAAD1 salt according to any of the embodiments described in the foregoing sections.

In another aspect, the invention provides methods of lowering blood glucose levels by administering to a subject (e.g., a human) a tris-ODAAD1 salt according to any of the embodiments described in the foregoing sections.

In another aspect, the invention provides methods of treating obesity by administering to a subject (e.g., a human) a tris-ODAAD1 salt according to any of the embodiments described in the foregoing sections.

In another aspect, the invention provides methods of slowing gastric emptying by administering to a subject (e.g., a human) a tris-ODAAD1 salt according to any of the embodiments described in the foregoing sections.

In another aspect, the invention provides methods of lowering an HbA1c level by administering to a subject (e.g., a human) a tris-ODAAD1 salt according to any of the embodiments described in the foregoing sections.

In another aspect, the invention provides methods of increasing glucose-dependent insulin secretion by administering to a subject (e.g., a human) a tris-ODAAD1 salt according to any of the embodiments described in the foregoing sections.

In another aspect, the invention provides methods of suppressing glucagon secretion by administering to a subject (e.g., a human) a tris-ODAAD1 salt according to any of the embodiments described in the foregoing sections.

In another aspect, the invention provides methods of treating an eating disorder by administering to a subject (e.g., a human) a tris-ODAAD1 salt according to any of the embodiments described in the foregoing sections.

In another aspect, the invention provides methods of modulating a human GLP1 receptor by administering to a subject (e.g., a human) a tris-ODAAD1 salt according to any of the embodiments described in the foregoing sections.

EXAMPLES

In the Examples below, the following compounds or compositions are recited. Their definitions are as follows.

ODAAD1 is (S)-3-(4'-cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid.

TWEEN 80 is a polyethylene sorbitol ester having a calculated molecular weight of 1,310 daltons, and available from Spectrum Chemicals, Gardena, Calif., USA.

HPMCAS is hydroxypropylmethyl cellulose acetate succinate.

AQOAT MG is a hydroxypropylmethyl cellulose acetate succinate binder available from Shinetsu Chemical Industries. Ltd., Tokyo, Japan.

AVICEL PH113 is a microcrystalline cellulose, and available from FMC Biopolymer, Newark, Del., USA.

KOLLIDON CL is a crospovidone, and available from BASF of Ludwigshafen, Germany.

CAB-O-SIL M5P is a colloidal silica, and available from Cabot of Tuscola, Ill., USA.

Starch 1500 LM is a starch, and is available from Colorcon of West Point, Pa., USA.

Example 1

Preparation of Tablet Containing Tris-ODAAD1 Salt 35.84 g of hydrochloride salt of ODAAD1 (1:1) is dissolved in 640 mL of acetone with stirring. While stirring the solution, 6.4 g of TWEEN 80 is added and allowed to dissolve. In a separate vessel, 8.96 g of tris(hydroxymethyl) aminomethane (tris) is dissolved in 18.0 mL of water. The aqueous solution of tris is then added to the ODAAD1 solution. The resulting mixture is stirred for 10 minutes. Precipitate is removed from the solution using a 24/40 filter funnel (Chemglass) with medium frit, under vacuum. Following initial collection of the precipitate, the precipitate is washed with 10 mL of acetone. To the filtered solution, 32.0 g HPMCAS (AQOAT MG) is added, and the solution is stirred until the HPMCAS dissolves. The resulting solution is spray dried in a spray dryer (Buchi B290 with high-efficiency cyclone and 1.5 mm nozzle). The conditions for the spray drying are: the aspirator is set to 100%, the inlet temperature is 80 ° C., the outlet temperature is 29 ° C., the nozzle pressure is 80 psig, and the fluid pump percentage is 75. The spray-dried material containing tris-ODAAD 1 salt is collected.

410.0 g of Starch 1500 LM is charged to a V-blender. Then, 1300 g of the spray-dried material containing the tris-ODAAD1 salt is added to the blender. Then, 325 g of crospovidone (KOLLIDON CL) is charged to the blender, and the resulting mixture is blended for 10 minutes. The resulting powder is removed from the blender and passed through a #30 mesh screen to obtain a solid blend containing a tris-ODAAD1 salt. 367.5 g of cellulose (AVICEL PH113) and 750 g of sodium carbonate (anhydrous, milled) are charged to the blender. To this mixture is added the solid blend containing a tris-ODAAD1 salt. Also, 750 g of sodium bicarbonate, 75.0 g of sodium lauryl sulfate, and 50.0 g of colloidal silica (CAB-O-SIL M5P) are added to the blender with the other solid ingredients. The resulting mixture is blended for 15 minutes. 15.0 g of the resulting blend is added to 15.0 g of magnesium stearate in a polyethylene bag and mixed for 2 minutes. The magnesium stearate blend is passed through a #30 mesh screen, and the magnesium stearate blend is added to the blender with the rest of the mixture containing the tris-ODAAD1 salt. The resulting mixture is blended for 5 minutes.

A compactor with rollers (smooth or grooved) is set up with a 1.25 mm screen on the granulator. The solid-state mixture is granulated into the roller compactor to form a continuous stream of brittle ribbon. Milled materials that pass through a #80 mesh hand screen are recirculated back to the roller compactor. The resulting granules are sifted through #30 mesh hand screen. The granules that are retained on the screen are passed through a Quadro Comil at 60% speed setting with 039R screen, and those granules are combined with the other granules to obtain a milled, compacted intragranular powder.

Half of the following ingredients are charged to the blender: 122.5 g of cellulose (AVICEL PH113), 270.0 g of crospovidone (KOLLIDON CL), 250.0 g of sodium carbonate (anhydrous, milled), 250.0 g of sodium bicarbonate, 135.0 g starch (Starch 1500 LM), and 375.0 g citric acid (anhydrous). Then, the milled, compacted intragranular powder is charged to the blender. Then the other half of the ingredients are added to the blender and the resulting mixture is blended for 15 minutes. 25.0 g of the resulting blend was added to 25.0 g of magnesium stearate in a PE bag and mixed for 2 minutes. The magnesium stearate blend was passed through a #30 mesh screen, and the magnesium stearate blend was added to the blender with the rest of the mixture containing the tris-ODAAD1 salt. The resulting mixture was blended for 5 minutes. The resulting powder is unloaded from the blender and compressed into tablets.

Example 2

Ingredients for Solid Composition Containing Tris-ODAAD1 Salt

A solid composition containing a tris-ODAAD 1 salt was prepared by a procedure similar to that described in Example 1. The resulting relative amounts of ingredients are as shown in Table 1 (in weight percent, based on the total weight of the solid composition).

TABLE 1

| Intragranular Ingredients | |
|---|---|
| Spray-dried evaporation residue containing tris-ODAAD1 salt, HPMCAS (1:1), TWEEN 80 | 23.8 |
| Microcrystalline Cellulose (AVICEL PH113) | 6.7 |
| Crospovidone (KOLLIDON CL) | 5.9 |
| Sodium Carbonate (anhydrous, milled) | 13.7 |
| Sodium Bicarbonate | 13.7 |
| Starch 1500 LM | 7.5 |
| Sodium Lauryl Sulfate | 1.4 |
| Colloidal Silica (CAB-O-SIL M5P) | 0.9 |
| Magnesium Stearate | 0.3 |
| Extragranular Ingredients | |
| Microcrystalline Cellulose (AVICEL PH113) | 2.2 |
| Crospovidone (KOLLIDON CL) | 4.9 |
| Sodium Carbonate (anhydrous, milled) | 4.6 |
| Sodium Bicarbonate | 4.6 |
| Starch 1500 LM | 2.5 |
| Citric Acid (anhydrous) | 6.9 |
| Magnesium Stearate | 0.5 |
| Total | 100.0 |

Example 3

Preparation of Tablet Containing Tris-ODAAD1 Salt 750 g of hydrochloride salt of ODAAD1 (1:1) is dissolved in 11.46 L of acetone with stirring. While stirring the solution, 140 g of TWEEN 80 is added and allowed to dissolve. In a separate vessel, 196 g of tris(hydroxymethyl)aminomethane (tris) is dissolved in 196 mL of water. The aqueous solution of tris is then added to the ODAAD1 solution. The resulting mixture is stirred for 10 minutes. Precipitate is removed from the solution using a 12 μm filter.

To the filtered solution, 701 g HPMCAS (AQOAT MG) is added, and the solution is stirred for about 1 hour to dissolve the HPMCAS. The resulting solution is spray dried in a spray dryer operating with 70° C. inlet temperature, 32° C. outlet temperature, and a Schlick high pressure nozzle under 50 bar pressure. The spray-dried material containing tris-ODAAD1 salt is collected.

287 g of pregelatinized maize starch (Starch 1500 LM) is passed through a 30-mesh sieve and charged to a 16-quart V-blender. Then, 875 g of the spray-dried material containing the tris-ODAAD1 salt is passed through a 30-mesh sieve and added to the blender. Then, 228 g of crospovidone (KOLLIDON CL) is passed through a 30-mesh sieve and charged to the blender, and the resulting mixture is blended for 10 minutes. The resulting powder is removed from the blender and passed through a #30 mesh screen to obtain a solid blend containing a tris-ODAAD1 salt. 303 g of microcrystalline cellulose (AVICEL PH113) is passed through a 30-mesh sieve and charged to a 16-quart V-blender. 525 g of sodium carbonate (anhydrous) is milled using a Quadro Comil operating at 1325 RPM fitted with a 610 μm screen and 0.250 inch spacer, and the milled powder is charged to the blender. To this mixture is added the solid blend containing a tris-ODAAD1 salt. 525 g of sodium bicarbonate is passed through a 30-mesh sieve and charged to the blender. 53 g of sodium lauryl sulfate is passed through a 30-mesh sieve and charged to the blender. 50.0 g of colloidal silicon dioxide (CAB-O-SIL M5P) is passed through a 30-mesh sieve and charged to the blender with the other solid ingredients. The resulting mixture is blended for 15 minutes. 11.0 g of the resulting blend is added to 11.0 g of magnesium stearate, pre-screened through a 30-mesh sieve, in a polyethylene bag and mixed for 2 minutes. The magnesium stearate blend is added to the blender with the rest of the mixture containing the tris-ODAAD1 salt. The resulting mixture is blended for 5 minutes.

A roller compactor with rollers (smooth or grooved) is set up with a screw speed of 70 RPM, a roller speed of 1.5 ROM, and a compaction pressure of 1700 psi. The solid-state mixture is fed into the roller compactor to form a continuous stream of brittle ribbon. The roller compacted material is sifted through an 80-mesh sieve, and milled materials that pass through a #80 mesh hand screen are recirculated back to the roller compactor. The compacted pre-blend retained on the 80-mesh sieve is milled using an oscillator fitted with a 16-mesh screen. The resulting granules are sifted through a 30-mesh hand screen. The granules that are retained on the screen are milled with a Quadro Comil at 60% speed setting with 039R screen, and those granules are combined with the other granules to obtain a milled, compacted intragranular powder.

Half of the following ingredients are charged to the blender: 86 g of microcrystalline cellulose (AVICEL PH113), 189 g of crospovidone (KOLLIDON CL), 175 g of sodium carbonate (anhydrous, milled), 175 g of sodium bicarbonate, 95 g of pregelatinized maize starch (Starch 1500 LM), and 263 g of citric acid (anhydrous). Then, the milled, compacted intragranular powder is charged to the blender. Then, the other half of the ingredients are added to the blender, and the resulting mixture is blended for 15 minutes. 17 g of magnesium stearate is passed through a 30-mesh sieve and mixed with 17 g of the resulting blend from above in a PE bag for 2 minutes. The magnesium stearate blend is again passed through a 30-mesh screen, and the magnesium stearate blend is added to a V-blender with the rest of the mixture containing the tris-ODAAD1 salt. The resulting mixture is blended for 5 minutes. The resulting powder is unloaded from the blender and compressed into tablets (about 1 gram in total weight).

Example 4

Preparation of Tablet Containing Tris-ODAAD1 Salt 327 g of pregelatinized maize starch (Starch 1500 LM) is passed through a 30-mesh sieve and charged to a 16-quart V-blender. Then, 438 g of the spray-dried material containing the tris-ODAAD1 salt (see Example 3) is passed through a 30-mesh sieve and added to the blender. Then, 267 g of crospovidone (KOLLIDON CL) is passed through a 30-mesh sieve and charged to the blender, and the resulting mixture is blended for 10 minutes. The resulting powder is removed from the blender and passed through a #30 mesh screen to obtain a solid blend containing a tris-ODAAD 1 salt.

292 g of microcrystalline cellulose (AVICEL PH113) is passed through a 30-mesh sieve and charged to a 16-quart V-blender. 565 g of sodium carbonate (anhydrous) is milled using a Quadro Comil operating at 1325 RPM fitted with a 610 μm screen and 0.250 inch spacer, and the milled powder is charged to the blender. To this mixture is added the solid blend containing a tris-ODAAD1 salt. 565 g of sodium bicarbonate is passed through a 30-mesh sieve and charged to the blender. 53.0 g of sodium lauryl sulfate is passed through a 30-mesh sieve and charged to the blender. 35.0 g of colloidal silicon dioxide (CAB-O-SIL M5P) is passed through a 30-mesh sieve and charged to the blender with the other solid ingredients. The resulting mixture is blended for 15 minutes. 11.0 g of the resulting blend is added to 11.0 g of magnesium stearate, pre-screened through a 30-mesh sieve, in a polyethylene bag and mixed for 2 minutes. The magnesium stearate blend is added to the blender with the rest of the mixture containing the tris-ODAAD1 salt. The resulting mixture is blended for 5 minutes.

A roller compactor with rollers (smooth or grooved) is set up with a screw speed of 70 RPM, a roller speed of 1.5 ROM, and a compaction pressure of 1700 psi. The solid-state mixture is fed into the roller compactor to form a continuous stream of brittle ribbon. The roller compacted material is sifted through an 80-mesh sieve, and the milled materials that pass through a #80 mesh hand screen are recirculated back to the roller compactor. The compacted pre-blend retained on the 80-mesh sieve is milled using an oscillator fitted with a 16-mesh screen. The resulting granules are sifted through a 30-mesh hand screen. The granules that are retained on the screen are milled with a Quadro Comil at 60% speed setting with 039R screen, and those granules are combined with the other granules to obtain a milled, compacted intragranular powder.

Half of the following ingredients are charged to the blender: 124 g of microcrystalline cellulose (AVICEL PH113), 229 g of crospovidone (KOLLIDON CL), 215 g of sodium carbonate (anhydrous, milled), 215 g of sodium bicarbonate, 134 g pregelatinized maize starch (Starch 1500 LM), and 301 g citric acid (anhydrous). Then, the milled, compacted intragranular powder is charged to the blender. Then the other half of the ingredients are added to the blender and the resulting mixture is blended for 15 minutes. 17.0 g magnesium stearate is passed through a 30-mesh sieve and mixed with 17.0 g of the resulting blend from above in a PE bag for 2 minutes. The magnesium stearate blend is again passed through a 30-mesh screen, and the magnesium stearate blend is added to a V-blender with the rest of the mixture containing the tris-ODAAD1 salt. The resulting mixture is blended for 5 minutes. The resulting powder is unloaded from the blender and compressed into 1082 mg tablets (total weight).

We claim:

1. A tris(hydroxymethyl)aminomethane salt of (S)-3-(4'-cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid.

2. The salt of claim 1, where the stoichiometric ratio of tris(hydroxymethyl)aminomethane to (S)-3-(4'-cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid in the salt is 1:1.

3. A solid composition comprising a tris(hydroxymethyl)aminomethane salt of (S)-3-(4'-cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid.

4. The solid composition of claim 3, where the stoichiometric ratio of tris(hydroxymethyl)aminomethane to (S)-3-(4'-cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid in the salt is 1:1.

5. The solid composition of claim 3, where the solid composition further comprises an evaporation residue.

6. The solid composition of claim 5, where the evaporation residue comprises at least a portion of the tris(hydroxymethyl)aminomethane salt of (S)-3-(4'-cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid.

7. The solid composition of claim 6, where the evaporation residue further comprises a binder.

8. The solid composition of claim 7, where the binder is selected from the group consisting of hydroxypropylmethyl cellulose acetate succinate (HPMCAS), polyvinylpyrrolidone (PVP), and hydroxypropylmethylcellulose (HPMC).

9. The solid composition of claim 8, where the binder is hydroxypropylmethyl cellulose acetate succinate (HPMCAS).

10. The solid composition of claim 7, where the evaporation residue further comprises a water-soluble surfactant.

11. The solid composition of claim 10, where the water-soluble surfactant is selected from the group consisting of a polyoxyethylene sorbitan fatty acid ester, sodium lauryl sulfate, and vitamin E d-alpha tocopheryl polyethyleneglycol succinate (vitamin E TPGS).

12. The solid composition of claim 11, where the water-soluble surfactant is a polyoxyethylene sorbitan fatty acid ester.

13. The solid composition of claim 6, where the solid composition further comprises a pharmaceutically acceptable basic excipient.

14. The solid composition of claim 13, where the pharmaceutically acceptable basic excipient is trisodium phosphate, potassium carbonate, sodium carbonate, sodium bicarbonate, potassium bicarbonate, or a mixture thereof.

15. The solid composition of claim 14, where the pharmaceutically acceptable basic excipient is a mixture of sodium carbonate and sodium bicarbonate.

16. A method of treating type 2 diabetes, of treating type I diabetes, of treating obesity, or lowering blood glucose, of slowing gastric emptying, of lowering an HbA1c level, of increasing glucose-dependent insulin secretion, of suppressing glucagon secretion, of treating an eating disorder, of modulating a human GLP1 receptor comprising administering to a subject a compound of claim 1.

17. A method of treating type 2 diabetes, of treating type I diabetes, of treating obesity, or lowering blood glucose, of slowing gastric emptying, of lowering an HbA1c level, of increasing glucose-dependent insulin secretion, of suppressing glucagon secretion, of treating an eating disorder, of modulating a human GLP1 receptor comprising administering to a subject a solid composition of claim 3.

18. A method of making a solid composition comprising:
mixing a binder and a tris(hydroxymethyl)aminomethane salt of (S)-3-(4'-cyano-biphenyl-4-yl)-2-{[(3R,7S)-3-[4-(3,4-dichloro-benzyloxy)-phenyl]-1-methyl-2-oxo-6-((S)-1-phenyl-propyl)-2,3,5,6,7,8-hexahydro-1H-4-oxa-1,6-diaza-anthracene-7-carbonyl]-amino}-propionic acid in a solvent to form a solution or suspension; and
removing the solvent from the solution or suspension.

19. The method of claim 18, wherein the step of removing the solvent comprising spray drying the solution or suspension to form a powder.

20. The method of claim 18, wherein the step of removing the solvent comprises spraying the solution or suspension onto a solid powder.

* * * * *